United States Patent [19]

Kato et al.

[11] Patent Number: 4,537,719
[45] Date of Patent: Aug. 27, 1985

[54] 4-METHYLSULFONYL-AZETIDINONE DERIVATIVES

[75] Inventors: Toshihisa Kato; Hisao Iwagami, both of Kawasaki; Naohiko Yasuda, Yokosuka, all of Japan

[73] Assignee: Ajinomoto Company Incorporated, Tokyo, Japan

[21] Appl. No.: 431,557

[22] Filed: Sep. 30, 1982

[30] Foreign Application Priority Data

Oct. 1, 1981 [JP] Japan .................... 56-156635

[51] Int. Cl.³ .................. C07D 205/08; C07D 403/12; A61K 31/495; A61K 31/395
[52] U.S. Cl. .................................... 260/239 A
[58] Field of Search ....................... 260/239 A

[56] References Cited

U.S. PATENT DOCUMENTS

| 4,138,486 | 2/1979 | Narisada et al. | 260/239 AL |
| 4,200,120 | 6/1980 | Hunt | 260/239 AL |
| 4,264,597 | 4/1981 | Hashimoto | 260/239 AL |

FOREIGN PATENT DOCUMENTS 2048261 12/1980 United Kingdom .

OTHER PUBLICATIONS

Kametani et al., J. C. S. Perkins I, 1981, p. 1884.

*Primary Examiner*—Mark L. Berch
*Attorney, Agent, or Firm*—Oblon, Fisher, Spivak, McClelland & Maier

[57] ABSTRACT

The present invention relates to novel azetidinone derivatives of the general formula:

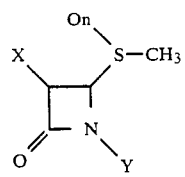

where
n is 0 or 2,
X is hydrogen, halogen, amino, alkylamino, benzylamino or acylamino, and
Y is

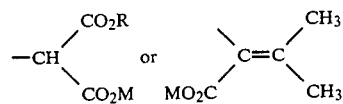

R is lower alkyl, 2,2,2-trichloroethyl, or aralkyl; and
M is hydrogen or alkali metal having $\beta$-lactamase inhibiting activity.

The derivatives of the present invention can be administered together with antibiotics having a $\beta$-lactam ring as antibacterial agents against $\beta$-lactamase producing bacteria.

A method for synthesizing said azetidinone derivatives is also disclosed.

6 Claims, No Drawings

4-METHYLSULFONYL-AZETIDINONE DERIVATIVES

BACKGROUND OF THE INVENTION

The present invention relates to novel azetidinone derivatives having β-lactamase inhibiting activity, and therefore useful as a β-lactamase inhibitor. Particularly, the azetidinone derivatives can be administered together with antibiotics having a β-lactam ring as antibacterial agents in order to prevent the ring from decomposing.

DESCRIPTION OF THE PRIOR ART

Of the most widely used antibiotics nowadays, penicillins such as benzyl penicillin (Penicillin G), phenoxymethyl penicillin (Penicillin V), Ampicillin, amoxicillin, carbenicillin and cephalosporins such as cephalothin, cephalexin, cefazolin have a β-lactam ring in the molecule. However, some of the above antibiotics do not show any antibacterial activity at all against some of the strains (bacteria).

The reason for this is thought to be that such bacteria produce an enzyme called β-lactamase, and the enzyme decomposes the β-lactam ring in penicillins or cephalosporins, thereby causing the penicillins or the cephalosporins to lose their antibacterial activity. Therefore, when a compound capable of inhibiting β-lactamase such as the ones mentioned above is used together with the penicillin or the cephalosporin, it works effectively against the bacteria.

DESCRIPTION OF THE PRESENT INVENTION

The present inventors developed useful β-lactamase inhibitors and succeeded in synthesizing novel azetidinone derivatives represented by the general formula:

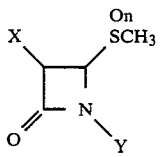

and further found that such derivatives have remarkable β-lactamase inhibiting activity. Based on them, this invention has been completed.

In the above general formula, n is an integer of 0 or 2, X is hydrogen, halogen such as chlorine and bromine, amino, alkylamino such as methylamino, ethylamino, benzylamino and dimethylamino, acylamino such as acetamide arylacetamide, 2-amino-2-arylacetamide, 2-acylamino-2-arylacetamide, and Y is

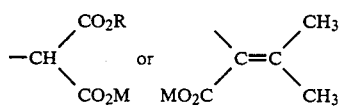

wherein R is lower alkyl with carbon numbers of 1 to 5, for example methyl, ethyl, isopropyl and t-butyl, aralkyl such as benzyl, and 2,2,2-trichloroethyl, and M is hydrogen and alkali metal such as sodium, potassium.

The derivatives of the present invention can enhance remarkably an antibacterial activity against β-lactamase-producing bacteria when they are used together with a penicillin or a cephalosporin.

The derivatives of the present invention represented by the above mentioned general formula, wherein n is an integer of 0, and Y is

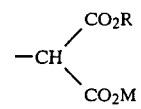

are produced by reacting 2-azetidinone derivatives represented by the general formula:

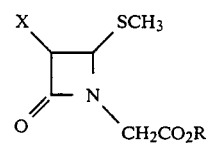

wherein X and R respectively have the same meanings as above, with benzyloxychloride in the presence of base to produce the intermediates represented by the general formula:

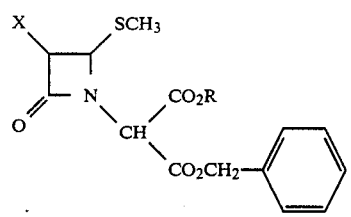

and reacting the intermediates (IV) with hydrogen to produce the intermediates.

In such case, n-butyllithium, lithium diisopropylamide, lithium hexamethyl disilazide, etc. are suitable for the base used in the reaction with the above mentioned carbobenzoxychloride. Particularly, lithium hexamethyldisilazide is more suitable.

The base is used in a ratio of 1 to 4, more preferably, 1.5 to 2.5 moles of the base per 1 mole of the above mentioned 2-azetidinone derivatives.

A solvent for the reaction is preferably an inactive organic solvent with a type of ether, and more preferably tetrahydrofuran, hereinafter referred to as "THF".

A temperature range for the reaction is between −78° and −30° C., more preferably between −60° and −78° C.

Under the above conditions the reaction is essentially carried out for not more than one hour, and thereby the thus obtained reaction solution is treated with an aqueous solution saturated with ammonium chloride. The organic layer is separated from the solution and the solvent is distilled off. The remaining substance is purified by chromatography on silica gel to give the object product. In order to obtain an object product from the above mentioned intermediate, the hydrogenation reaction is carried out at a temperature between 0° and 25° C. for 5 minutes to 2 hours in an atmosphere of hydrogen under a pressure of 1 to 10 atm. in the solvent such as ethyl acetate, ether, dioxane, THF, methanol, ethanol in the presence of catalyst for hydrogenation such as platinum metal, oxide thereof 10% Pd/C or 30% Pd in BaCO₃.

The derivatives of the present invention wherein n is 2, represented by the general formula:

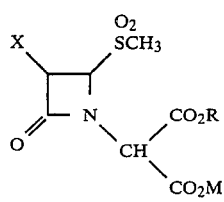

V wherein X, R and M have respectively the same meanings as above, can be produced by treating the above mentioned intermediates (IV) with an oxidizing agent to give the second derivatives represented by the general formula:

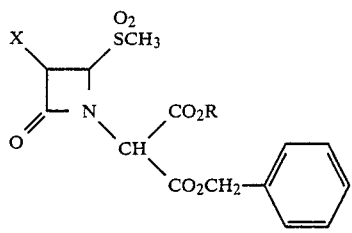

VI and hydrogenating a second derivatives in a solvent such as ethyl acetate, ether, dioxane, THF, methanol, and ethanol in the presence of catalyst for hydrogenation such as platinum metal, oxide thereof, 10% Pd/C and 30% Pd in BaCO$_3$ at a temperature of 0° to 25° C. for 5 minutes to 2 hours in an atmosphere of hydrogen under a pressure of 1 to 10 atm.

The following oxidizing agents are preferably employed; for oxidation of the above mentioned intermediates, permanganate, organic acids, etc and particularly, sodium permanganate, potassium permanganate, 3-chloroperoxybenzoic acid, and peracetic acid are more preferably employed. These oxidizing agents are used in a ratio of 2.0 to 4.0 moles of the oxidizing agents per one mole of the above mentioned intermediates.

In case of oxidation with an organic peracid, particularly 3-chloroperbenzoic acid is preferably employed, and for the solvent, for example, chlorinated hydrocarbons such as dichloromethane, chloroform and 1,2-dichloroethane, and ethers such as diethyl ether, THF, and 1,2-dimethoxyethane are employed. In such case, the reaction for oxidation is usually carried out at a temperature of −20° to 50° C., more preferably, 0° to 20° C. The reaction is usually completed in 2 to 20 hours or so.

The thus obtained reaction solution is filtrated, and the object product is obtained by chromatography on silica gel.

The derivatives of the present invention represented by the above mentioned general formula (I), the derivatives wherein n is an integer of 2 and Y is

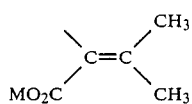

that is, the compounds represented by the general formula:

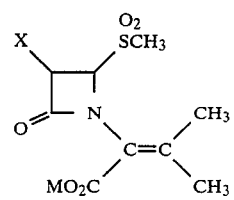

VII wherein X and M have respectively the same meanings as above, are produced by hydrogenating the compounds represented by the general formula:

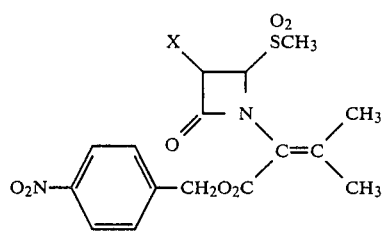

VIII in the solvent such as dioxane, THF, methanol and ethanol in the presence of catalyst such as platinum metal, oxides thereof, 10% Pd/C and 30% Pd in BaCO at a temperature of 0° to 25° C. for 5 minutes to 2 hours at an atmosphere of hydrogen under 1 to 10 atm.

Examples of the derivatives for the present invention thus obtained are as follows:

(3R,4R)-1-(1-carboxy-2-methylprope-1-nyl)-4-methylsulfonyl-3-[D-(−)-α-aminophenylacetamide]-2-azetidinone (IX)

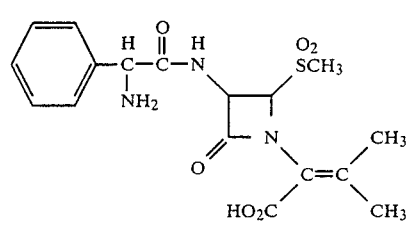

IX (3R,4R)-1-(1-carboxy-2-methylprope-1-nyl)-4-methylsulfonyl-3-amino-2-azetidinone (X)

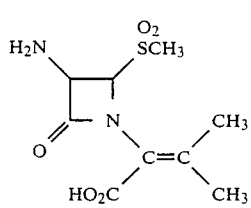

X

(3R,4R)-1-(1-carboxy-2-methylprope-1-nyl)-4-methylsulfonyl-3-[D(−)-α-(4-ethyl-2,3-dioxo-1-piperazine-carboxamide)-α-(4-hydroxyphenyl)acetamide]-2-azetidinone (XI)

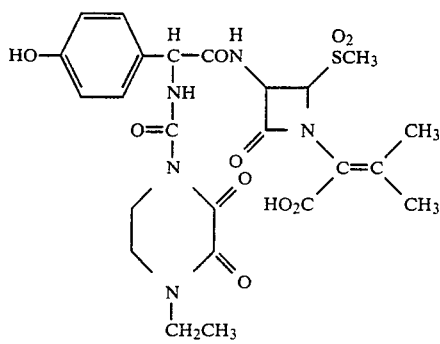

In the present invention, a free form of the derivatives can be converted to the alkali metal salts such as sodium, or potassium salt thereof by neutralization with base, when necessary.

By elementary analysis, IR spectrum, NMR spectrum, etc., it was confirmed that the derivatives have the above mentioned chemical structures.

The present invention will be explained precisely in the following Examples.

EXAMPLES

EXAMPLE 1

Production of 1-(1-benzyloxycarbonyl-1-methoxycarbonylmethyl)-4-methylthio-2-azetidinone:

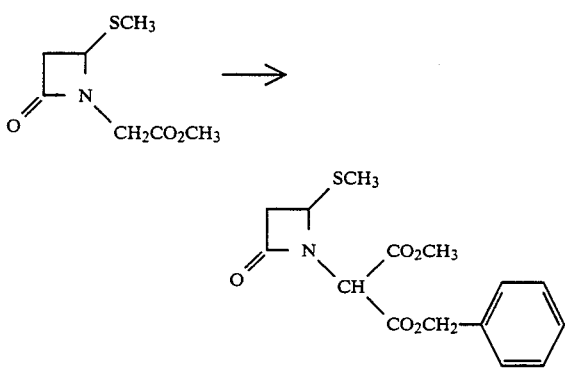

To solution of hexamethyldisilazane (6.6 ml, 32 mM) in the tetrahydrofuran (100 ml), which had been distilled in the presence of lithium aluminium hydride (LiAlH$_4$) at −78° C. while stirring, n-butyllithium (2.05 g, 32 mM) n-hexan solution (1.6M, 20 ml) was added. Hereinafter, tetrahydrofuran is referred to as THF.

After 30 minutes from the addition of n-butyllithium solution, 1-methoxycarbonylmethyl-4-methylthio-2-azetidinone (3 g, 16 mM) THF(20 ml) solution was added thereto dropwisely in 5 minutes and thus obtained mixture was stirred for 15 minutes. To this solution carbobenzoxychloride (3.2 g, 19 mM) THF(20 ml) solution was added dropwisely in 10 minutes and thus obtained mixture was stirred for 1 hour at −78° C.

The solution was warmed to a room temperature in 2 hours, and an aqueous solution saturated with ammonium chloride was added thereto. The aqueous mixture was extracted three 100 ml portions of ethyl acetate.

The extracted organic layer was washed with 10% sodium chloride aqueous solution and dried. An oily substance containing the object product was given by evaporating the solvent. This substance was purified by silica gel chromatography with 30% ethyl acetate in n-hexan to obtain the object product in an oily state (yield: 3.18 g, 62%).

NMR spectrum (CDCl$_3$): ppm 2.02 (S, 1.5H), 2.04 (S, 1.5H), 3.20 (m, 2H), 3.75 (S, 1.5H), 3.77 (S, 1.5H), 5.10 (m, 2H), 5.25 (S, 2H), 7.35 (S, 5H).

EXAMPLE 2

Production of 1-(1-carboxy-1-methyoxycarbonylmethyl)-4-methylthio-2-azetidinone:

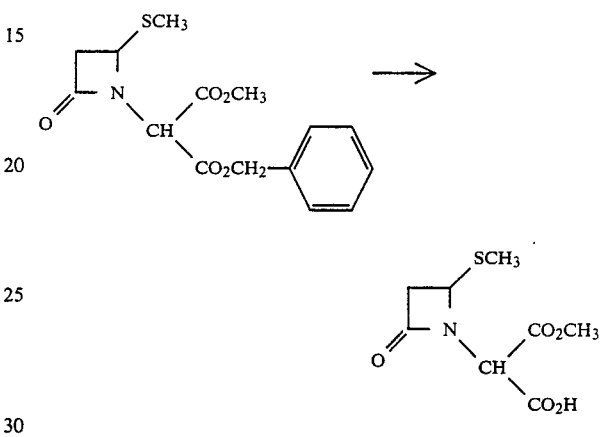

1-(1-benzyloxycarbonyl-1-methoxycarbonylmethyl)-4-methylthio-2-azetidinone (2 g) was dissolved in a mixture of THF (30 ml) and water (30 ml). Thereto hydrogen addition was carried out in the presence of 30% Pd in BaCO$_3$ catalyst (5 g) for 50 minutes under ordinary pressure.

To the mixture diatomaceous earth was added, and thus obtained mixture was filtered off. THF was distilled under a reduced pressure at not more than 30° C. This aqueous solution was adjusted to pH 7.0 and washed with ethyl acetate (20 ml). The aqueous layer was adjusted to pH 2.0∼2.5 with 1N hydrochloric acid and was extracted three 100 ml portions of ethyl acetate. The above all organic layers were mixed together and dried with magnesium sulfate. Therefrom ethyl acetate was distilled to obtain the object product (yield: 1.1 g, 76%).

NMR spectrum (CDCl$_3$): ppm 2.15 (S, 3H), 3.30 (m, 2H), 3.84 (S, 3H), 5.15 (m, 2H), 8.75 (S, 1H).

EXAMPLE 3

Production of 1-(1-benzyloxycarbonyl-1-methoxycarbonylmethyl)-4-methylsulfonyl-2-azetidinone:

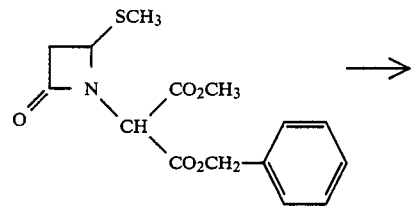

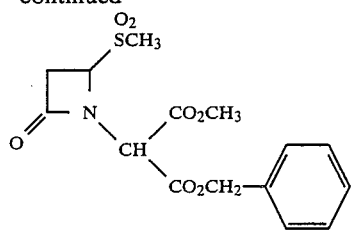

1-(1-benzyloxycarbonyl-1-methoxycarbonylmethyl)-4-methylthio-2-azetidinone (3.0 g, 9.3 mM) was dissolved in chloroform (30 ml), and to this mixture 3-chloroperoxybenzoic acid (4 g, 23 mM) was added in 10 minutes at 0° C. It was stirred for 3 hours at between 0° and 5° C., and then purified by silica gel chromatography with 5% ethyl acetate in n-hexan to obtain the object product in an oily state (yield: 2.47 g, 75%).

NMR spectrum (CDCl$_3$): ppm 2.98 (S, 1.5H), 3.00 (S, 1.5H), 3.40 (m, 2H), 3.80 (S, 3H), 5.15 (m, 2H), 5.28 (S, 2H), 7.40 (S, 5H).

EXAMPLE 4

Production of 1-(1-carboxy-1-methoxycarbonylmethyl)-4-methylsulfonyl-2-azetidinone:

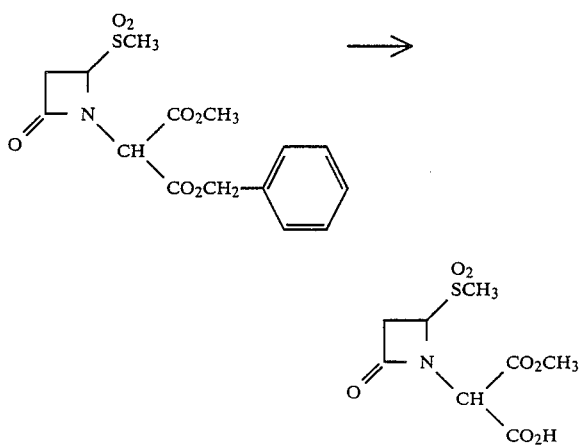

1-(1-benzyloxycarbonyl-1-methoxycarbonylmethyl)-4-methylsulfonyl-2-azetidinone (1 g) was dissolved in a mixture of THF (20 ml) and water (20 ml), and then reacted with hydrogen for hydrogen addition thereto in the presence of 30% Pd in BaCO$_3$ catalyst (4.0 g) for 1 hour under an ordinary pressure.

To this mixture diatomaceous earth was added, and thus obtained mixture was filtered off. THF was distilled under a reduced pressure by means of evaporator. This aqueous solution was adjusted to pH 7.0 and was washed with ethyl acetate (20 ml), and again was adjusted to pH 2.0 to 2.5 with 1N hydrochloric acid. Therefrom ethyl acetate was distilled to obtain the object product in an oily state (yield: 0.45 g, 60%).

NMR spectrum (CDCl$_3$): ppm 3.00 (S, 3H), 3.40 (m, 2H), 3.78 (S, 3H), 4.90 (m, 1H)

EXAMPLE 5

Production of (3R,4R)-1-(1-carboxy-2-methylprope-1-nyl)-4-methylsulfonyl-3-[D(—)-α-aminophenylacetamido]-2-azetidinone:

(1) Production of (3R,4R)-1-(1-p-nitrobenzyloxycarbonyl-2-methylprope-1-nyl)-4-methylsulfonyl-3-amino-2-azetidinone

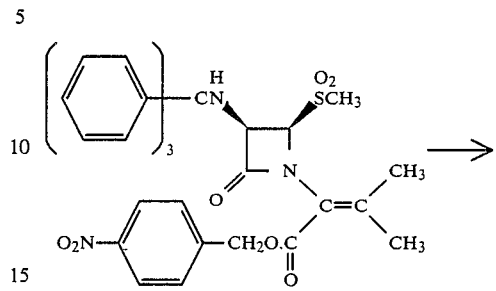

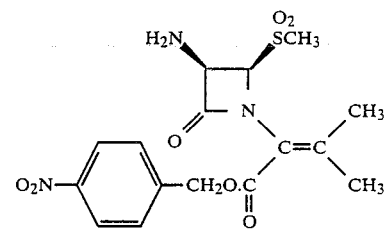

(3R, 4R)-1-(1-p-nitrobenzyloxycarbonyl-2-methylprope-1-nyl)-4-methylsulfonyl-3-triphenylmethylamino-2-azetidinone (3.105 g, 5.0 mM) was dissolved in acetone (50 ml), to this solution in an ice bath p-toluenesulfonic acid 1 hydrate (1.425 g, 7.5 mM) was added, and the mixture was stirred at room temperature overnight.

After the reaction solution was concentrated, to the residue ethyl acetate (50 ml) and water (50 ml) were added. By adjusting the aqueous solution to pH 7.0, the solution had two layers. The aqueous layer was further extracted with ethyl acetate (2×50 ml). All the extracted ethyl acetate solutions were mixed together and the mixture was washed with brine. The ethyl acetate solution was dried with anhydrous magnesium sulfate. The solution was distilled off in vacuo, to give an oily residue, which was subjected to chromatography on silica gel (100 g). Elution with n-hexane-ethyl acetate (1:1) afforded the title compound as colourless crystals (yield: 1.36 g, 72%).

NMR spectrum (CDCl$_3$, added with D$_2$O): ppm 2.17 (S, 3H), 2.27 (S, 3H), 2.99 (S, 3H), 4.56 (d, 1H, J=5.0 Hz), 5.00 (d, 1H, J=5.0 Hz), 5.31 (S, 2H), 7.53 (d, 2H), 8.26 (d, 2H).

(2) Production of (3R,4R)-1-(1-p-nitrobenzyloxycarbonyl-2-methylprope-1-nyl)-4-methylsulfonyl-3-[D(—)-α-t-butoxycarbonylaminophenylacetamid]-2-azetidinone:

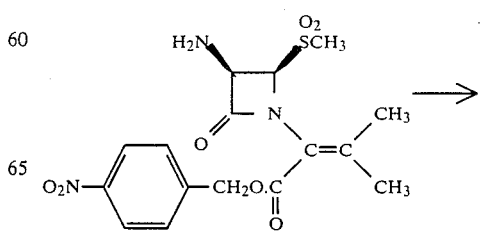

-continued

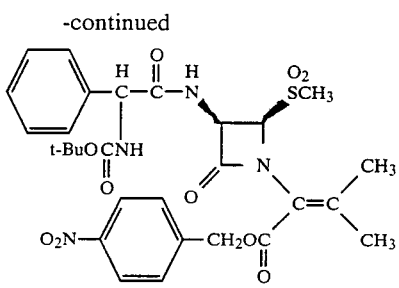

(3R,4R)-1-(1-p-nitrobenzyloxycarbonyl-2-methyl-prope-1-nyl)-4-methylsulfonyl-3-amino-2-azetidinone (948 mg, 2.5 mM) was dissolved in THF (20 mg) and thereto D-N-t-butoxycarbonyl-phenylglycine (1.26 g, 5.0 mM) dissolved in THF (10 ml) was added. To this mixture, further, 1-ethoxycarbonyl-2-ethoxy-1,2-dihydroquinoline (1.24 g, 5.0 mM) was added and thus obtained mixture was stirred for 16 h at room temperature.

The solvent was removed in vacuo to give an oily residue, which was subjected to chromatography or silica gel (100 g). Elulion with n-hexane-ethyl acetate (1:1) afforded the title compound as a colorless amorphous solid (yield: 1.11 g, 72%).

NMR spectrum (CDCl$_3$): ppm 1.39 (S, 9H), 2.13 (S, 3H), 2.29 (S, 3H), 2.36 (S, 3H), 5.16 (d, 1H), 5.29 (S, 2H), 5.68~5.94 (m, 2H), 7.38 (s, 5H), 7.50 (d, 2H), 8.23 (D, 2H).

(3) Production of (3R,4R)-1-(1-carboxy-2-methyl-prope-1-nyl)-4-methylsulfonyl-3-[D-(−)-α-amino-phenylacetamide]-2-azetidinone

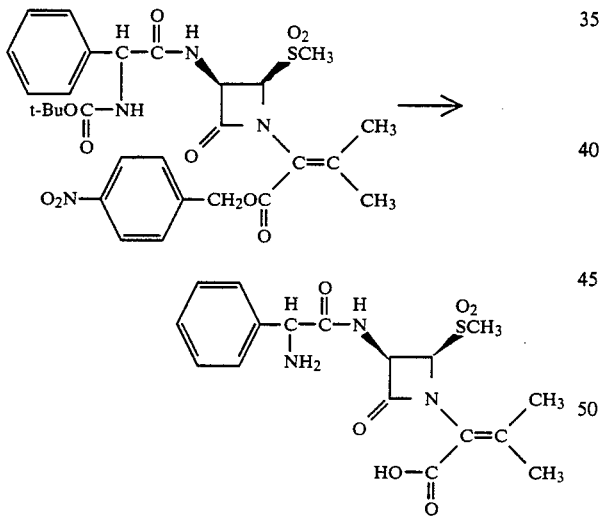

30% Pd in BaCO$_3$ (2.2 g) was suspended in a phosphate buffer solution (pH 7.0, 50 ml) and stirred vigorously under a current of hydrogen (1.0 atm) for 1.5 h. To this mixture (3R,4R)-1-(1-p-nitrobenzyloxycarbonyl-methylpropenyl)-4-methylsulfonyl-3-[D-(−)-t-butoxycarbonylamionophenylacetamide]-2-azetidinone (1.11 g, 1.79 mM) dissolved in THF (30 ml) was added at a time, and the mixture was stirred vigorously under a current of hydrogen (1.0 atm) for 3.3 h.

After the reaction was finished, the reaction solution was filtered using celite. After filtration, the celite was washed with methanol (30 ml) and then water (30 ml). These obtained methanol solution and water solution were added to the filtrate. This solution was evaporated in vacuo to remove THF and methanol.

Thus obtained aqueous solution was adjusted to pH 1.5 with 5N phosphoric acid and then was extracted with ethyl acetate (2×50 ml).

All of the organic layers were mixed together, washed with brine, and dried with anhydrous magnesium sulfate. Therefrom the solvent and removed in vacuo to give (3R,4R)-1-(1-carboxy-2-methylprope-1-nyl)-4-methylsulfonyl-3-[D-(−)-t-butoxycabonylaminophenylacetamide]-2-azetidinone as an oily syrup. This product gave only one spot with R$_f$=0.11 as detected by means of UV in TLC using a mixture of ethyl acetate, n-hexan and acetic acid (25:25:1) as an eluent.

To (3R,4R)-1-(1-carboxy-2-methylprope-1-nyl)-4-methylsulfonyl-3-[D-(−)-t-butoxycarbonylaminophenylacetamide]-2-azetidinone as obtained above, trifluoroacetic acid (16.7 ml) and anisole (2 ml) were added while cooling in an ice bath, and thus obtained mixture was stirred for 1 h also while cooling in the ice bath.

After the completion of the reaction, the mixture was evaporated in vacuo and to thus obtained oily residue ether (30 ml) was added to give a powder. The powder was separated by filtration and was washed well with ether, and then, was dissolved in water (50 ml) at once. The solution was adjusted to pH 6.80 with Amberlite IR-45 (hydroxide form). The used resin was removed by filtration, and remaining filtrate was lyophilized to give the title compound (yield 380 mg, 56%).

NMR spectrum (D$_2$O): ppm 1.88 (S, 3H), 2.05 (S, 3H), 2.61 (S, 3H), 5.16 (S, 1H), 5.28 (d, 1H, J=4.9 Hz), 5.87 (d, 1H, J=4.9 Hz), 7.52 (S, 5H).

EXAMPLE 6

Production of (3R, 4R)-1-(1-carboxy-2-methylprope-1-nyl)-4-methylsulfonyl-3-amino-2-azetidinone:

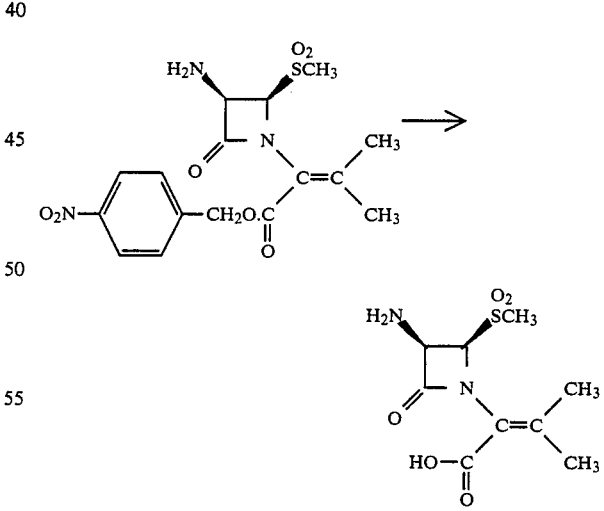

30% Pd in BaCO$_3$ (780 mg) was suspended in water (30 ml) and the mixture was stirred vigorously under a current of hydrogen (1.0 atm) for 2 h. To this mixture, (3R,4R)-1-(1-p-nitrobenzyloxycarbonyl-2-methyl-prope-1-nyl)-4-methylsulfonyl-3-amino-2-azetidinone (390 mg, 1.03 mM) dissolved in THF (30 ml) was added at a time, and was stirred vigorously under a current of hydrogen (1.0 atm) for 3 h.

After the reaction was finished, the used catalyst was removed by filtration by means of celite. After the filtration, the celite was washed with methanol (20 ml) and with water (20 ml). Thus obtained methanol solution and water solution were added to the filtrate. This solution was concentrated in vacuo to remove THF and methanol, and then, lyophilized to give the title compound (yield: 122 mg, 49%).

NMR spectrum (D₂O): ppm 1.92 (S, 3H), 2.06 (S, 3H), 3.11 (S, 3H), 4.88 (d, 1H, J=5.0 Hz), 5.24 (d, 1H, J=5.0 Hz).

EXAMPLE 7

Production of (3R,4R)-1-(1-carboxy-2-methylprope-1-nyl)-4-methylsulfonyl-3-[D(—)1-α-(4-ethyl-2,3-dioxo-1-piperazinecarboxamide)-α-(4-hydroxyphenyl-)acetamide]-2-azetidinone sodium salt:

(1) Production of (3R,4R)-1-(1-p-nitrobenzyloxycarbonyl-2-methylprope-1-nyl)-4-methylsulfonyl-3-[D(—)-α-(4-ethyl-2,3-dioxo-1-pirazine-carboxamide]-α-(4-hydroxyphenyl)acetamide]-2-azetidinone

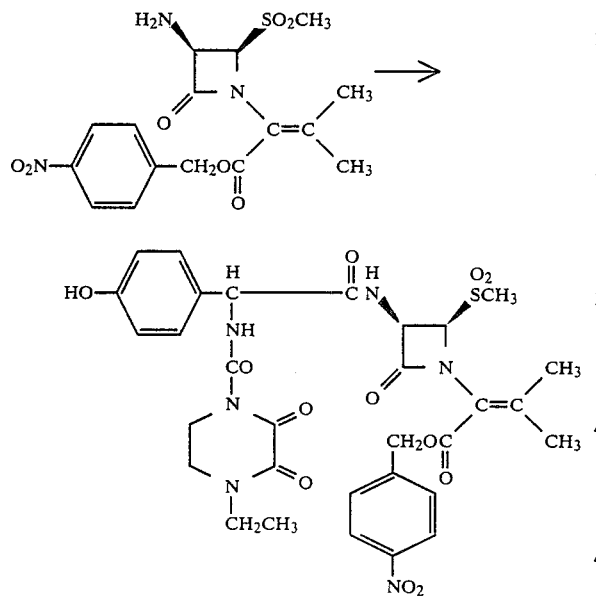

(3R,4R)-1-(1-p-nitrobenzyloxcarbonyl-2-methyl-prope-1-nyl)-4-methysulfonyl-3-amino-2-azetidinone (750 mg, 1.98 mM) was dissolved in THF (20 ml), and thereto D(—)-α-(4-ethyl-2,3-dioxo-1-piperazine-carboxamide)-α-(4-hydroxyphenyl) acetic acid (1.34 g, 4.0 mM) and 1-ethoxycarbonyl-2-ethoxy-1,2-dihydroquinoline(989 mg, 4.0 mM) were added. Thus obtained mixture was stirred for 16 h at room temperature.

After the reaction finished, the reaction solution was concentrated in vacuo to give an oily residue, which was subjected to chromatography on silicagel (100 g). Elution with n-hexane-ethyl acetate (1:1) afforded the title compound (yield: 590 mg, 44%).

NMR spectrum (d⁶-DMSO): ppm 1.10 (t, 3H), 2.07 (S, 3H), 2.20 (S, 3H), 2.29 (S, 3H), 3.09 (q, 2H), 3.4~3.6 (m, 2H), 3.8~4.0 (m, 2H), 5.36 (S, 2H), 5.38 (d, 1H), 5.5~5.7 (m, 2H), 6.74 (d, 2H), 7.28 (d, 2H), 7.67 (d, 2H), 8.26 (d, 2H), 9.22 (d, 1H), 9.15 (S, 1H), 9.77 (d, 1H).

(2) Production of (3R,4R)-1-(1-carboxy-2-methyl-prope-1-nyl)-4-methylsulfonyl-3-[D(—)-α-(4-ethyl-2,3-dioxo-1-piperazine carboxamide)-α-(4-hydroxyphenyl-)acetamide]-2-azetidinone sodium salt

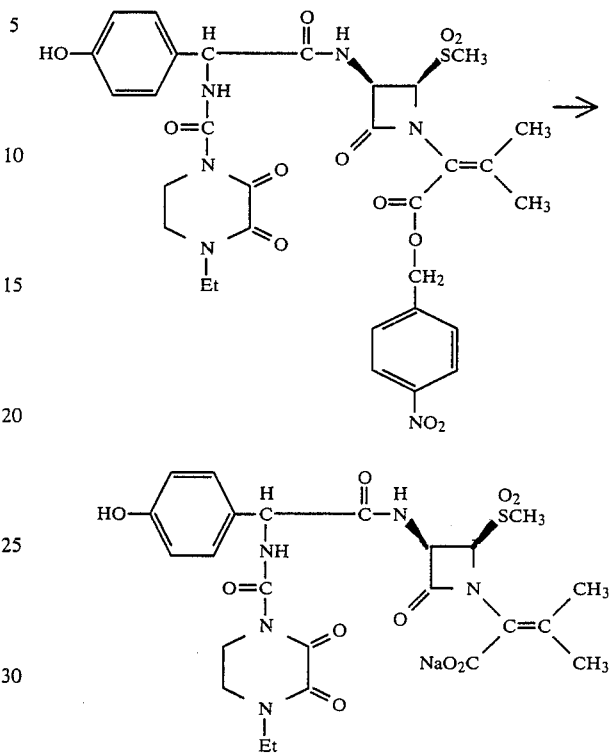

30% Pd in BaCO₃ (1.2 g) was suspended in water (30 ml), and sodium hydrogencarbonate (73 mg, 0.87 mM) was added thereto. This mixture was stirred vigorously under a current of hydrogen (1.0 atm) for 1.25 h.

To thus obtained mixture, (3R,4R)-1-(1-p-nitrobenzyloxycarbonyl-2-methylprope-1-nyl)-4-methylsulfonyl-3-[D(—)-α-(4-ethyl-2,3-dioxo-1-piperazine carboxamide]-α-(4-hydroxyphenyl)acetamide-2-azetidine (590 mg, 0.87 mM) dissolved in THF (30 ml) was added at a time and then the mixture was vigorously stirred under a current of hydrogen (1.0 atm) for 4 h.

After the reaction finished, the reaction mixture was filtrated using celite. After the filtration the celite was washed with water (50 ml) and with methanol (50 ml). Thus obtained water solution and methanol solution were added to the filtrate. This mixture was concentrated in vacuo to remove THF and methanol, and was lyophilized to give the title compound (yield: 430 mg, 88%).

NMR spectrum (D₂O): ppm 1.22 (t, 3H), 1.91 (S, 3H), 2.08 (S, 3H), 2.54 (S, 3H), 3.50 (q, 2H), 3.5~3.7 (m, 2H), 3.85~4.05 (m, 2H), 5.29 (d, 1H, J=4.5 Hz), 5.42 (S, 1H), 5.84 (d, 1H, J=4.5 Hz), 6.91 (d, 2H, J=8.4 Hz), 7.35 (d, 2H, J=8.4 Hz).

Experiment

A phosphate buffer solution (pH 7.0, 0.5M, 0.2 ml), a sample*, which is a β-lactamase inhibiting agent, dissolved in the same buffer solution as mentioned above, and water (10 ml) were put in a test tube. In this tube, ampicillin (2 mM, 0.2 ml) in the case of penicillinase, and cephaloridine (2 mM, 0.2 ml) in the case of cephalosporinase, were added. This mixture was stirred moderately for 5 minutes at 30° C. in a thermostat.

Microbial cells producing β-lactamase were collected, washed and suspended in the same buffer solution as above and thereto a β-lactamase solution (0.1 ml) obtained by destruction of the microbial cells with ultrasonic waves was added and reacted for 20 minutes.

The reaction was stopped by adding sodium tungstate (0.15M, pH 4.0, 1 ml) and an iodo reagent (3 ml) having iodine (0.1 mM), potassium iodide (1.6 mM) and 0.4% starch solution, (pH 6.0) was added thereto and was allowed to stand for 20 minutes. The absorbance was determined at 575 nm.

On the other hand, the same experiment as above without the sample (Control) was carried out and the absorbances were determined in the same manner as above.

From each determined value as obtained above, the difference between the absorbance of the blank and that of the sample, referred to as As, and the difference between the absorbance of the blank and that of the Control referred to as AB were obtained, and therefrom the inhibiting ratio was calculated by the following equation:

Inhibiting Ratio(%) = (AS/AB) × 100

Some of the results as obtained above, in which Enterobacter cloacae was used as the β-lactamase-producing microorganism was used are as follows:

| Sample No.* | Inhibiting Ratio (%) |
|---|---|
| 1 | 46.2 |
| 2 | 51.4 |
| 3 | 27.6 |
| 4 | 35.8 |

*Sample:
1: N—(1-carboxyl-1-methoxycarbonylmethyl)-4-methylthio-2-azetidinone
2: N—(1-carboxy-1-methoxycarbonylmethyl)-4-methylsulfonyl-2-azetidinone
3: (3R, 4R)-1-(1-carboxy-2-methylprope-1-nyl)-4-methylsulfonyl-3-[D(−)-α-aminophenylacetamide]-2-azetidinone
4: (3R, 4R)-1-(1-carboxy-2-methylprope-1-nyl)-4-methylsulfonyl-3-amino-2-azetidinone

What is claimed is:

1. Azetidinone derivatives represented by the formula:

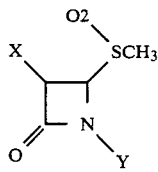

wherein
X is hydrogen, halogen, amino, methylamino, ethylamino, benzylamino, dimethylamino or acylamino selected from the group consisting of acetamide, arylacetamide, 2-amino-2-arylacetamide, 2-acylamino-2-arylacetamide, or D(−)1-α-(4-ethyl-2,3-dioxo-1-piperazinecarboxamide)-α-(4-hydroxyphenyl)acetamide); and
Y is

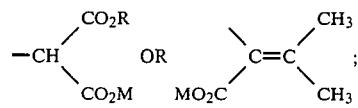

wherein R is lower alkyl, benzyl, or 2,2,2-trichloroethyl, and M is hydrogen or alkali metal.

2. Azetidine derivatives as claimed in claim 1, wherein X is:
hydrogen,
bromine, chlorine, amino, methylamino, ethylamino, benzylamino, dimethylamino,
acetamide, arylacetamide, 2-amino-2-arylacetamide, 2-acylamino-2-arylacetamide, or
D(−)1-α-[4-ethyl-2,3-dioxo-1piperazine-carboxamide)-α-(4-hydroxyphenyl)acetamide];
R is:
lower alkyl with carbon numbers 1 to 5 such as methyl, ethyl, n-propyl, isopropyl, n-butyl, ter-butyl,
benzyl or 2,2,2-trichloroethyl; and
M is:
hydrogen, sodium or potassium.

3. The azetidinone derivatives of claim 1, wherein Y is:

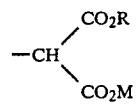

4. The azetidinone derivatives of claim 3, wherein X is:
hydrogen,
bromine, chlorine,
amino, methylamino, ethylamino, benzylamino, dimethylamino,
acetamide arylacetamide, 2-amino-2-arylacetamide, 2-acylamino-2-arylacetamide, or
D(−)1-α[4-ethyl-2,3-dioxo-1-piperazinecarboxamide-α-(4-hydroxyphenyl)acetamide];
R is:
lower alkyl with carbon numbers 1 to 5 selected from the group consisting of methyl, ethyl, n-propyl, isopropyl, n-butyl, ter-butyl,
benzyl and 2,2,2-trichloroethyl; and
M is:
hydrogen, sodium or potassium.

5. The azetidinone derivatives of claim 1 being N-(1-carboxy-1-methoxycarbonylmethyl)-4-methylsulfonyl-2-azetidinone.

6. The azetidinone derivatives of claim 1 being (3R,4R)-1-(1-carboxy-2-methylprope-1nyl)-4-methylsulfonyl-3-amino-2-azetidinone.

* * * * *